Figure 1:
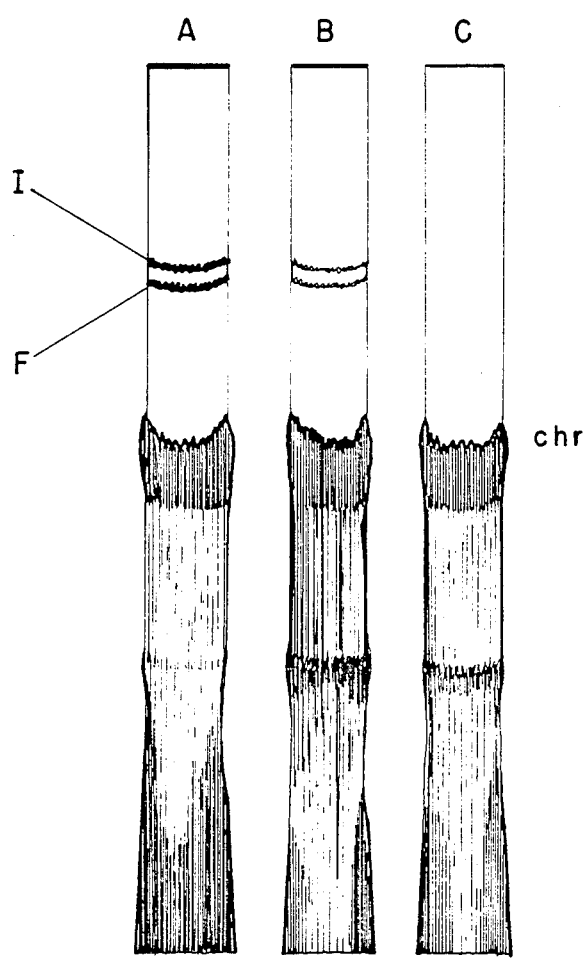

United States Patent [19]

Formal et al.

[11] Patent Number: 4,632,830
[45] Date of Patent: Dec. 30, 1986

[54] ORAL VACCINE FOR IMMUNIZATION AGAINST ENTERIC DISEASE

[75] Inventors: Samuel B. Formal, Kensington; Louis S. Baron, Silver Spring; Dennis J. Kopecko, Rockville, all of Md.

[73] Assignee: The United States of America as represented by the Secretary of the Army, Washington, D.C.

[21] Appl. No.: 289,013

[22] Filed: Jul. 31, 1981

[51] Int. Cl.$^4$ .................. A61K 39/112; C12N 1/20
[52] U.S. Cl. ............................ 424/92; 424/93; 435/253
[58] Field of Search ............... 424/92, 93; 435/253, 435/172, 172.3

[56] References Cited

U.S. PATENT DOCUMENTS 3,856,935 12/1972 Germanier ..................... 424/92

OTHER PUBLICATIONS

Kopecko, D., et al., Injection and Immunity, vol. 29, pp. 207–214, 1980.

Primary Examiner—Blondel Hazel
Attorney, Agent, or Firm—John H. Raubitschek; John M. Petruncio; Werten F. W. Bellamy

[57] ABSTRACT

A living, attenuated, oral vaccine system is described for the immunization against enteric disease. This oral vaccine is a genetic hybrid derivative of an attenuated galactose epimeraseless strain of S. typhi which carries at least one protective antigen other than normal somatic S. typhi antigens. The oral vaccine can provide protection against both typhoid fever and at least one other enteric disease. A bivalent oral vaccine is described wherein the non-typhoid protective antigen is the plasmid-encoded form I antigen of Shigella sonnei. A protective antigen from Shigella sonnei was transferred to a streptomycin resistant mutant of S. typhi strain Ty21a. The transconjugant S. typhi strain expressed both S. typhi and S. sonnei antigens and protected experimental animals against lethal infections with either S. typhi or S. sonnei. This strain is considered to be useful as a vaccine against typhoid fever and bacillary dysentery caused by S. sonnei. The mutated galactose epimeraseless S. typhi strain such as S. typhi Ty21a strain can be utilized as a carrier strain for other protective antigens.

7 Claims, 2 Drawing Figures

ORAL VACCINE FOR IMMUNIZATION AGAINST ENTERIC DISEASE

BACKGROUND OF THE INVENTION

This invention relates broadly to a class of oral vaccines for the prevention of enteric disease. A living, non-pathogenic mutant, oral vaccine strain of *Salmonella typhi* has already been shown to be safe and effective in protecting against typhoid fever; it is a mutant, galactose epimeraseless strain of *S. typhi* designated as Ty21a. Its preparation, safety, and efficacy as an oral vaccine have already been described in Germanier, R. and Furer, J. Infect. Dis. 131:553–558, 1975; Wahdan, N. H. et al., Bull. WHO. 58:469–474; and U.S. Pat. No. 3,856,935 to R. Germanier, the disclosure of which is hereby incorporated by reference.

Bacterial diseases of the gastrointestinal tract usually occur by one of three overall mechanisms. The first mechanism, termed "intoxication," occurs by bacterial secretion of an exotoxin that oftentimes is preformed in food prior to ingestion by the host. This process is exemplified by staphylococcal or clostridial food poisoning. In contrast, the remaining two processes require living and multiplying disease agents. In the "enterotoxigenic" mechanism, bacteria colonize the small intestine, usually in the jejunum or duodenum. These bacteria multiply on the intestinal surface and elaborate an enterotoxin that stimulates excessive fluid and electrolyte efflux resulting in a watery diarrhea. Enterotoxigenic *Escherichia coli* and *Vibrio cholera* serve as typical examples. Finally, a third group of organisms, termed "invasive," actually penetrate the epithelial mucosa of the large intestine. Subsequently, these organisms multiply intracellularly and disseminate within or through the mucosa. This latter mechanism, classically typified by Shigella and Salmonella, is now thought to be used by invasive strains of *E. coli*, Yersinia, and, possibly, Campylobacter. In contrast to other invasive bacterial diseases like salmonellosis, in which the invading bacteria are disseminated throughout the host, shigellosis is a disease normally confined to the intestinal lining. Thus, these features distinguish the toxigenic from the invasive mechanism of intestinal disease.

Two common and essential features of invasive bacteria are their ability to penetrate and to multiply within the epithelial cells of the colon. Mutants of Shigella strains that fail to penetrate or that penetrate but cannot multiply intracellularly have been isolated. Both types of mutants are avirulent. The process of invasion has thus far been characterized in microscopic, but not biochemical detail. The first visible alteration in the host intestinal epithelium is a localized destruction of the microvilli, the outermost structure of the intestinal lining. The invading bacteria are then engulfed by means of an invagination of the intestinal cell membrane and are contained intracellularly within vacuoles. Subsequently, the microvilli are reestablished and intracellular bacterial multiplication occurs. These bacterial then destroy the vacuole and disseminate to adjacent cells, causing necrosis and resulting in acute inflammation and focal ulceration of the epithelium. The resulting dysentery is characterized by a painful, bloody, and mucous diarrhea, normally of relatively small volume.

Genetic studies of *Shigella flexneri* have previously resulted in the conclusion that virulence is multideterminant, with at least two widely separated bacterial chromosomal regions being required for invasion. Furthermore, these studies have shown that not only is a smooth lipopolysaccharide bacterial cell surface necessary for intestinal invasion, but also that only certain O-repeat unit polymers are effective in this process; this is true for both shigellae and invasive *E. coli*. Until recently, plasmids did not appear to play a role in the invasion process or in the virulence of Shigella. Recent evidence amassed over the past three years, however, demonstrates that plasmids of Shigella are involved in the invasion process.

Bacillary dysentery remains highly endemic in many areas of the world and still is a significant cause of illness in developed countries. There are over thirty serotypes of the organisms which cause shigellosis (bacillary dysentery), the prominent members of which are *S. sonnei*, *S. flexneri*, *S. dysenteriae* and *S. boydii*. There are six serologically separable *S. flexneri* types (i.e. I through VI) of which *S. flexneri* types IIa and III are responsible for the majority of *S. flexneri* infections. In the United States and northern Europe, *S. sonnei* is responsible for more than 65 percent of the cases. Together with *S. flexneri* IIa and III strains, *S. sonnei* strains cause greater than 90% of all shigellosis worldwide. Parenteral vaccines have not been effective in protecting against bacillary dysentery because shigellosis is an infection limited to the superficial layer of the colonic mucosa. It is, therefore, not surprising that attempts to immunize man or other primates with killed vaccines or even living virulent organisms, administered by the parenteral route, have not been successful.

Living, attenuated, oral Shigella strain vaccines have been demonstrated to be protective against bacillary dysentery under both laboratory and field conditions. It has been suggested that the local intestinal immune response which is induced by the living oral vaccines inhibits invasion of intestinal epithelial cells by the pathogen. This immunity has been associated with the type-specific somatic antigen of the vaccine strain. None have come into widespread use because of difficulties in isolating safe, genetically-stable (non-reverting) strains or because of the large number of doses required to produce immunity.

*S. sonnei* produce a characteristic cell surface antigen, termed form I, which has altruonic acid as a component of its O-specific side chain. Recently, it has been demonstrated that the form I antigen is encoded by a large non-conjugative plasmid (Kopecko, D. J. et al., Infect. Immun. 29:207–214, 1980). This fundamental study found that by utilizing a plasmid mobilizing system, transfer of the form I antigen synthesizing genes was possible to certain specific *Shigella flexneri* and *Salmonella typhi* strains, or retransfer to a form II *S. sonnei* strain was possible.

Unlike shigellae, the typhoid bacillus causes a systemic infection following penetration of the intestinal mucosa, and parenteral vaccines have been shown to be effective against this infection. These parenteral vaccines do, however, elicit significant side effects which include fever, malaise, headache, and localized reactions at the site of inoculation. Since the safety (i.e., freedom from the above-mentioned side effects) and immunogenicity of *S. typhi* strain Ty21a has been established, it was considered that this attenuated strain might be utilized as a carrier organism for other protective antigens and, thus, could be used as an oral vaccine to protect against an enteric infection other than typhoid fever or simultaneously against both typhoid fever and also other enteric infections. By protective antigen we mean a molecular structure, either somatic or soluble, which stimulates production of one or more antibodies and protects against a specific enteric disease. Additionally, the term "carries", "carried" or "carrier" is not to be construed as limiting the invention to a specific derivative or method of modification of the parent galE *S. typhi* strain. The term does not imply that the genetic determinant necessarily has to be plasmid-borne; conversely, it can be part of the bacterial chromosome.

DESCRIPTION OF THE INVENTION

This invention is directed to a living, attenuated, oral vaccine capable of immunizing against only a single (non-typhoid) enteric disease or simultaneously against more than one enteric disease. It is recognized that shigellosis can be caused by any one of four distinct species and in the context of this invention may be considered four separate enteric diseases. The invention is based on an attenuated galactose epimeraseless strain of *Salmonella typhi*, proven to be safe for prevention of typhoid fever, which has been genetically engineered to carry the genetic determinants of additional protective antigens. In addition to typhoid fever, enteric infections caused by other organisms are considered amenable to treatment with a vaccine according to this invention; e.g., these organisms include various Shigella strains such as *S. sonnei, S. flexneri, S. dysenteriae, S. boydii* as well as enterotoxogenic *Escherichia coli, Vibrio cholera,* and Yersinia. Enteric disease caused by bacterial secretion of an exotoxin exemplified by staphylococcal or clostridial food poisoning are also considered amenable to treatment with a vaccine according to this invention. To construct an *S. typhi* hybrid vaccine that is protective against staphylococcal or similar exotoxin, one approach consists of transferring mutant exotoxin genes to the galE *S. typhi* strain, so that a toxoid (i.e., nontoxic variant antigen) is produced which will stimulate the production of antibodies effective against the specific native exotoxin. The concept also applies to enterotoxigenic *E. coli* and *Vibrio cholera* enterotoxins. Also vaccines predicated on modification of the galE mutant strain of *S. typhi* by the introduction of antigens from enteric viruses, like rotavirus, are considered within the scope of this invention.

A particular vaccine of interest according to this invention is a living, attenuated, oral vaccine to be used to protect against both typhoid fever and bacillary dysentery due to *S. sonnei.* As mentioned above, the synthesis of the form I protective antigen of *Shigella sonnei* is encoded for on a large non-conjugative plasmid (Kopecko, D. J. et al., Infect. Immun. 29:207–214, 1980). This plasmid was transferred to a streptomycin-resistant mutant of the attenuated *S. typhi*Ty21a vaccine strain. The resulting transconjugant strain 5076-1-C (on deposit at the American Type Culture Collection, Rockville, Md. —ATCC No. 31904) expresses the somatic antigens of both *S. typhi* and *S. sonnei* form I. The transconjugant strain produced antibodies in rabbits to both *S. typhi* and *S. sonnei* and this strain also protected mice against intraperitoneal challenge with either virulent *S. typhi* or *S. sonnei* cells. Strain 5076-1-C is considered to be a candidate, attenuated, oral vaccine strain which is intended to protect against both clinical typhoid fever and bacillary dysentery due to *S. sonnei.*

CONSTRUCTION OF THE DONOR STRAIN

The $F'_{ts}$lac::Tn3 plasmid was introduced into *Shigella sonnei* I strain 53G by mating this strain with *E. coli* strain HU 679. The mating was incubated at 32° C. and clones were selected and purified on a minimal growth medium supplemented with lactose, nicotinic acid aspartic acid, and 20 micrograms per milliliter ampicillin. One resulting lactose-utilizing (Lac+) and ampicillin resistant $Ap^R$clone was grown in Penassay broth (Difco) at 42° C. to eliminate the F'lac plasmid. Sixteen $Ap^R$, Lac−form I 53G independent isolates were selected on MacConkey agar containing 20 μ/ml ampicillin. These 16 clones which now contain Tn3 were remated with *E. coli strain HU*679, to regain the F'lac::Tn3 plasmid. Stable Lac+*S. sonnei* form I clones, containing F'lac::Tn3, from these matings were tested for their ability to transfer the form I antigen (along with the Lac+marker) to the recipient form II *S. sonnei* strain, which is lac−, met−, nic−, $nal^R$. Conjugal mating mixtures were plated on minimal growth medium supplemented with lactose, nicotinic acid, aspartic acid, methionine, and 50 μ/ml nalidixic acid. One donor strain (5006-7-3) was observed to transfer form I-synthesizing ability. One resulting clone (5022-1C-9) was then used as a donor organism to transfer the form I antigen to *S. flexneri* IIa strain M42-43. Mating mixtures of strains 5022-1C-9 and M42-43 were plated on mininal growth medium supplemented with lactose, nicotinic acid and aspartic acid. A resulting isolate of *S. flexneri,* strain 5054-6-1, which inherited the form I antigen was employed as the donor strain to transfer the form I antigen to *Salmonella typhi* strain Ty21a.

RECIPIENT STRAIN

*Salmonella typhi* strain Ty21a which is commercially available under the mark VIVOTIF was obtained by L. S. Baron from R. Germanier of the Swiss Serum Institute, Berne, Switzerland, the assignee of U.S. Pat. No. 3,856,935 to Germanier. For experimental purposes, a streptomycin resistant mutant of this strain was obtained by mutagenesis. The desirable carrier characteristics of the parent galactose empimeraseless mutant *S. typhi* Ty21a strain were retained while allowing for experimental selection.

CONSTRUCTION OF THE *S.* I TRANSCONJUGANT STRAIN 5076-1C

Donor strain 5054-6-1 (*S. flexneri* harboring the *S. sonnei* form I plasmid) was mated with the streptomycin resistant mutant of *S. typhi* strain Ty 21a. Approximately $1\times10^9$ donor and $1\times10^{10}$ recipient cells were mixed on the surface of a minimal agar growth medium supplemented with lactose, tryptophan, cystine, casamino acids and streptomycin.

Lac+*S. typhi* transconjugants were selected on an appropriate minimal agar growth medium. The resulting Lac+clones were repurified by restreaking twice on identical medium and, then, were examined serologically. One Lac+ *isolate, designated strain* 5076-1C, which was agglutinated by both *S. typhi* and *S. sonnei* form I antisera, was selected for further study. This strain was found to have the serological characteristics of the recipient *S. typhi* Ty21a strain and also expressed the *S. sonnei* form I antigen.

The *S. typhi* transconjugant 5076-1C was expected to have received both $F'_{ts}$lac::Tn3 mobilizing plasmid and the form I plasmid. To demonstrate the presence of these plasmids in strain 5076-1C, plasmid DNA was prepared from the donor, recipient, and transconjugant strains. A comparison of the plasmid content of the parental and transconjugant strains was made by examination of their plasmid profiles following agarose gel electrophoresis. FIG. 1 shows the agarose gel electrophoretic profiles of circular plasmid DNA obtained from the recipient *S. typhi*-Ty21a, the donor *S. flexneri* 5054-6-1, and the transconjugant from I *S. typhi* 5076-1C strains. This figure shows the plasmid profile of: (A) donor strain 5054-6-1; (B) transconjugant *S. typhi* strain 5076-1C; and (C) recipient *S. typhi* Ty21a strain. The gel position expected for fragmented or chromosomal DNA is indicated by "Chr". The positions of supercoiled molecules of the F'$_{ts}$lac::Tn3 plasmid and the form I plasmid are indicated by an "F" and an "I", respectively. Some small plasmid DNA species can be seen below the chromosomal band. The direction of electrophoresis is from top to bottom. As shown in FIG. 1, the recipient *S. typhi* Ty21a strain contains no large plasmids. However, both the donor and transconjugant strains can be seen harboring two large plasmid species, which correspond to the independent F'$_{ts}$lac::Tn3 (80 Mdal) and form I (120 Mdal) plasmids. These observations suggest that form I antigen synthesis in the *S. typhi* transconjugant strain 5076-1C is due to the presence of the form 1 plasmid.

SEROLOGICAL CHARACTERIZATION OF FORM I-GALE *S.* DERIVATIVE STRAIN 5076-1C

Figure 2:
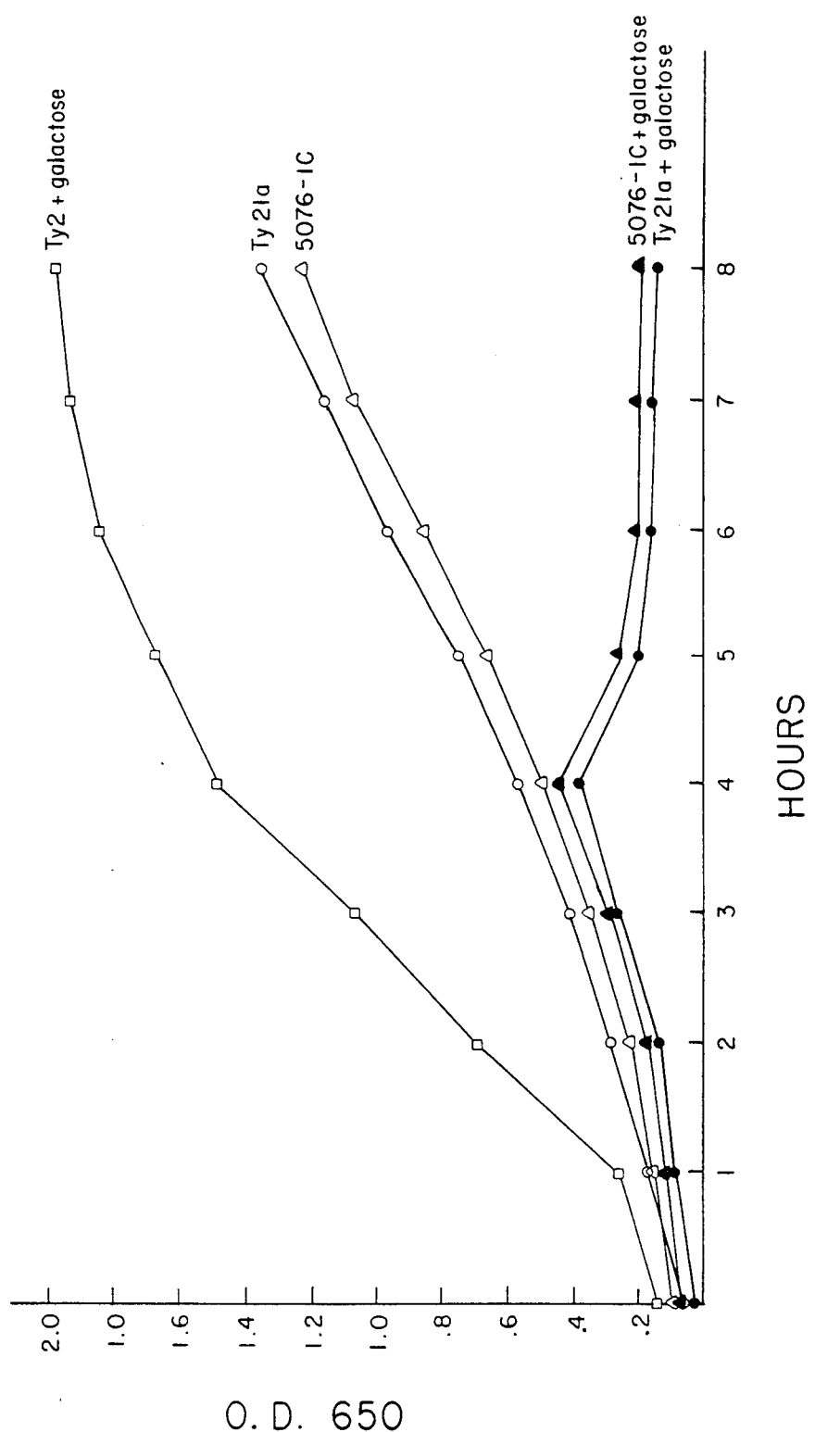

As shown in Table 1, the *S. typhi* transconjugant strain 5076-1C was agglutinated to high titer both by *S. typhi* antisera and by *S. sonnei* form I specific antisera. Furthermore, an antiserum prepared against the *S. typhi* galE, form I strain 5076-1C, was observed to agglutinate both *S. typhi* and *S. sonnei* form I cells. As expected, *S. typhi* Ty21a or 643W cells failed to agglutinate in *S. sonnei* form I antiserum and neither *S. sonnei* form I 53G cells nor the *S. flexneri* - form I donor strain, 5054-6-1, reacted in *S. typhi* antiserum.

resulst in cell lysis. The growth patterns of *S. typhi* strains Ty21a and 5076-1C, when grown in BHI broth in the presence or absence of 0.1% galactose, are shown in FIG. 2. FIG. 2 shows the sensitivity of *S. typhi* strains Ty2, Ty21a and 5076-1C to growth in the presence or absence of galactose. The strains were grown in BHI with (closed symbols) or without (open symbols) 0.1% galactose. The control Gal+strain Ty2 grew equally well in both media. Both strains are similarly inhibited by the presence of galactose in the medium, relative to the control Gal+*S. typhi* strain Ty2 which is not inhibited by galactose. Thus, strain 5076-1C behaves identical to the Ty21a strain under these conditions.

PERSISTENCE IN MOUSE TISSUE OF PARENTAL AND TRANSCONJUGANT GALE *S. typhi* STRAINS Cells of *S. typhi* Ty21a and the transconjugant form I strain 5076-1C were each injected IP into separate groups of 18 mice. Three animals were sacrificed at intervals of up to 15 days post-inoculation and the spleens were checked for the presence of bacteria. All animals harbored viable cells of either organism when the animals were sacrificed after 1 to 3 days post-inoculation. However, cultures of subsequently sacrificed animals were uniformly negative.

To test the safety of slightly larger doses of these vaccine strains, groups of 5 mice were injected IP with $1 \times 10^8$ cells of either *S. typhi* Ty21a or the derivative strain 5076-1C, suspended in hog gastric mucin. All animals survived during the one week observation period. Therefore, both the parental and transconjugant form I galE *S. typhi* strains behaved as expected, i.e., viable cells do not persist in infected mice for longer than 3 to 6 days.

MOUSE PROTECTION STUDIES

Viable cells of *S. typhi* Ty21a, *S. sonnei* 53G form I, and *S. typhi* galE, form I strain 5076-1C, as well as the standard acetone-killed and dried (AKD) *S. typhi* Ty2

TABLE 1

Agglutinin and Agglutinin Adsorption Studies With the Parental and Derivative *S. Typhi* and *S. Sonnei* Strains

| | Unabsorbed Antisera | | | Antisera absorbed with strain 5076-1C cells | |
|---|---|---|---|---|---|
| Antigen | *S. typhi* 643W | *S. sonnei* I | 5076-1C | *S. typhi* 643W | *S. sonnei* I |
| *S. typhi* Ty21a | 2560* | <80 | 1600 | 160 | ND** |
| *S. typhi* 643W | 2560 | <80 | 1600 | 160 | ND |
| *S. sonnei* 53G | <80 | 640 | 400 | ND | <80 |
| *S. flexueri* 5054-6-1 | <80 | 640 | 400 | ND | <80 |
| *S. typhi*-form I 5076-1C | 2560 | 640 | 1600 | <80 | <80 |

*Reciprocal of the dilution in which agglutination was observed
**ND = Not done

In further studies, adsorption, of *S. sonnei* form I specific antiserum with cells of the *S. typhi* - form I strain 5076-1C reduced the titer against *S. sonnei* form I strain 53G to <1:80. Similarly, adsorption of *S. typhi* 643W antiserum with the form I *S. typhi* 5076-1C cells lowered the titer against cells of *S. typhi* 643W from 1:1600 to 1:160. Thus, the *S. typhi* galE, form I strain 5076-1C produces both the normal *S. typhi* somatic antigens as well as the *S. sonnei* form I antigen.

GALACTOSE-INDUCED SENSITIVITY TO LYSIS

*S. typhi* strain Ty21a contains A galE mutation that, following galactose uptake and the intracellular accumulation of galactrose-1-phosphate and UDP-galactose, cells were used to immunize mice, by either the IP or SC route. Control mice received inocula of saline. All mice were challenged 4 weeks post-immunization with either virulent *S. typhi* or *S. sonnei* cells and deaths were recorded after 72 hrs. The results of these studies are summarized in Table 2. Each of the monovalent vaccines protected against homologous, but not against heterologous challenge. In contrast, the form I *S. typhi* Ty21a derivative strain 5076-1C protected against challenge with either *S. typhi* or *S. sonnei*.

TABLE 2

Protection of Mice Against *S. Typhi* and *S. Sonnei* Challenge With *S. Typhi* and *S. Sonnei* Vaccines

| Vaccine | Route of Immuni-zation | Challenge Strain* S. typhi TY2 | S. sonnei 53GI |
|---|---|---|---|
| Living *S. typhi* TY21a | IP | 0/12** | 15/15 |
|  | SC | 0/15 | 15/15 |
| Living *S. typhi*-form I 5076-1C | IP | 0/13 | 1/14 |
|  | SC | 1/16 | 0/16 |
| Living *S. sonnei*-53GI | IP | 14/16 | 1/16 |
|  | SC | 16/16 | 0/16 |
| AKD*** *S.typhi* TY2 | IP | 2/16 | 15/16 |
|  | SC | 1/16 | 16/16 |
| Saline | IP | 10/10 | 10/10 |

*Challenges, suspended in 0.5 percent hog gastric mucin, were administered IP.
** $\frac{\text{Deaths}}{\text{Total}}$ recorded 72 hrs after challenge
***Standard acetone-killed and dried typhoid vaccine

CONSTRUCTION OF ADDITIONAL GALE *S. typhi* GENETIC HYBRID STRANS FOR USE AS ORAL VACCINES The general usefulness of the galE *S. typhi* mutant as a protective antigen carrier for oral vaccine strain construction is further shown by the following experiments. *Shigella flexneri* serotype IIa possesses cell surface antigens that are coded for by the bacterial chromosome. Previous studies have revealed that the group antigenic determinants are closely linked to the his region, while the type antigenic determinants are located close to the pro region of the chromosome. An F'lac plasmid carrying the bacteriophage Mu cts 62 was introduced into *S. flexneri* IIa strain M4243 and the resultant strain, termed 6023-1-1, was maintained at 32° C., so as not to induce the Mu phage. Strain 6023-1-1 was conjugally mated at 37° C. with an *Escherichia coli* strain that was recA, mel, his, leu, met, arg, nal$^R$ and a Mu cts 62 lysogen. Growth at 37° C. would be expected to induce the Mu phage and cause transposition of the his region of the chromosome to the F'lac plasmid. Selection was made for an *E. coli* transconjugant that had received a F'lac-Mu plasmid that had picked up the *S. flexneri* IIa histidine genes and presumably the closely linked group antigenic genes. A His+ transconjugant was isolated and this strain expressed the *S. flexneri* group (3, 4) cell surface antigens. This *E. coli* DK102 transconjugant strain was used as a door to transfer the F'lac-Mu-his plasmid into a mutant of the *S. typhi* TY21a strain. The *S. typhi* TY21a strain was made Str$^R$ and His− (i.e., constructed by nitrosoguanidine mutagenesis and penicillin selection) and a Mu cts 62 lysogen. The resulting *S. typhi* transconjugant strain carrying the F'lac-Mu-his plasmid was found to express both the *S. typhi* 9, 12 antigens and the *S. flexneri* gp. 3, 4 antigens thus indicating that this *S. typhi* hybrid strain (designated WR6003) would serve as an oral vaccine for immunization against disease caused by either *S. typhi* or *S. flexneri* IIa organisms. A oral vaccine strain considered a better vaccine candidate against *S. flexneri* IIa than WR6003 has been constructed.

In experiments similar to those described immediately above again using the donor strain 6023-1-1, both the his and pro regions of the *S. flexneri* IIa chromosome were transferred, presumably via a recombinant F'lac/Mu-his-pro plasmid, into an intermediate *E. coli* strain, Mu cts 62 lysogen of AB1133 pro, his, thr, leu, thi, arg. This intermediate strain was then used to transfer the *S. flexneri* his and pro regions to a Mu cts 62 lysogenic, his$^{132}$, str$^R$ mutant of *S. typhi* TY21a. The resulting galE *S. typhi* hybrid strain expressed both the *S. typhi* 9, 12 antigens and the *S. flexneri* type II and group (3, 4) antigens. This hybrid strain is considered an oral vaccine candidate that will protect against typhoid fever and shigellosis due to *S. flexneri* IIa. This hybrid oral vaccine strain, WR6000, has been deposited with the ATCC (ATCC No. 31931).

The various *S. typhi* genetic hybrid oral vaccine strains whose construction has been described above (i.e., 5076-1C, WR6003, and WR6000) are considered exemplary of useful strains according to this invention. The 5076-1C *S. typhi* hybrid strain carrying the *S. sonnei* form I plasmid is genetically unstable due to the natural instability of the form I plasmid. Although the 5076-1C strain is useful, the construction of more stable hybrid strains is desirable. It is important to emphasize that genetic hybrids of *S. typhi* can be constructed by use of procedures, e.g., recombinant DNA procedures, other than standard classical genetic manipulation. Recombinant DNA techniques can be employed to make a desirable *S. typhi* galE strain carrying the *S. sonnei* form I antigenic determinants. The form I genes of *S. sonnei* can simply be isolated and spliced, via known recombinant DNA techniques, into a small, genetically stable plasmid which can then be inserted into the galE *S. typhi* strain. The resulting hybrid is considered desirable because of the stable form I antigen expression.

In addition, known recombination DNA procedures can be employed in the construction of a variety of other galE *S. typhi* oral vaccine strains according to further aspects of this invention. Exemplary of such strains using the *S. typhi* galE oral vaccine strain as a carrier of non-typhoid protective antigens are those involving non-typhoid protective antigens of *Vibrio cholera* and enterotoxigenic *e. coli*. *Vibrio cholera* and exterotoxigenic *E. coli* are responsible for a large proportion of diarrheal disease worldwide. The genes for heat labile enterotoxin (LT) synthesis in *E. coli* have been found to be plasmid-encoded (Smith, H. W., and M. Lingood. 1971, J. Med. Microbiol. 4: 301–305). *E. coli* LT appears to be functionally and immunologically similar to the enterotoxin of *vibrio cholera*. (Smith, N. W., and R. B. Sack. 1973, J. Infect. Dis. 127: 164–170). These enterotoxins are comprised of two subunits, a toxigenic and an immunogenic component. *E. coli* LT genes have been isolated and characterized by recombinant DNA procedures (Dallas, W. S. et. al., 1979, J. Bacteriol. 139:850–858). A multivalent vaccine according to this invention can be constructed by using currently available experimental techniques; the genes for the immunogenic component (i.e., nontoxigenic portion) of *E. coli* LT can be isolated on a small recombinant plasmid. The resulting plasmid, when inserted into a galE *S. typhi* strain, will produce the immunogenic portion of *e. coli* heat labile enterotoxin. This soluble protective antigen is expected to induce immunity to enteric diseases caused by both LT[30] *E. coli* and toxigenic *Vibrio cholera*. Thus, the resulting galE *S. typhi* hybrid strain is considered the essential component of an oral vaccine which will protect against typhoid fever and diarrheal diseases caused by *Vibrio cholera* and LT+ *E. coli*. It should be noted that the immunogenic component of LT toxin is considered to be a soluble antigen, as opposed to the attached somatic antigens. By using similar techniques in accordance with the description of this invention additional galE *S. typhi* oral vaccine strains carrying antigens from a variety of bacterial, viral, or other enteric disease agents can be constructed.

It should be noted that many animals (e.g., calves, pigs, rabbits and sheep) are susceptible to diarrheal diseases caused by a variety of enteric disease agents (e.g. enterotoxigenic *Escherichia coli* strains). These diarrheal diseases cause an enormous death rate among neonatal animals, especially in animal rearing facilities. Although *Salmonella typhi* infections do not cause classical typhoid fever in these animal hosts, it is possible that galE *S. typhi* genetic hybrid strains could be used to immunize these animals for protection against one or more different enteric diseases.

The galE *S. typhi* genetic hybrid strains, discussed herein, are the active agents or components in preparation designed for use as oral vaccines according to this invention. These galE *S. typhi* genetic hybrid cells can be dispersed in a pharmaceutical diluent such as a liquid suitable for ingestion by a human or lower animal host. Alternatively, the hybrid vaccine cells can be freeze-dried and administered in a solid form (e.g. as a tablet or capsule).

There may be physical limitations to the number of non-typhoid antigenic genes that can be introduced into a single galE *S. typhi* strain. However, this invention provides for a multivalent vaccine, protective simultaneously against several diseases, which can be constructed by mixing several different *S. typhi* genetic hybrid strains, each one producing different non-typhoid protective antigens. For example, according to this invention three different galE. *S. typhi* hybrid strains, each considered protective against typhoid fever and a different Shigella strain, can be constructed. One hybrid strain produces the *S. sonnei* form I antigen, a second hybrid strain produces the *S. flexneri* IIa somatic antigens and the third hybrid strain produces the *S. flexneri* III somatic antigens. Since *S. sonnei* and *S. flexneri* serotypes IIa and III are responsible for greater than ninety percent of all shigellosis worldwide, this vaccine is highly desirable.

The invention described herein is directed to a galE *S. typhi* genetic hybrid strain, expressing at least one non-typhoid protective antigen, that can be used in an oral vaccine for immunization against enteric disease. The genetic manipulation of non-typhoid protective antigenic genes and their transfer to the galE *S. typhi* carrier strain can be effected by a variety of procedures. The F'lac::T3 and F'$_{ts}$lac::Mu cts62 plasmids were employed in the construction of the genetic hybrid strains discussed above. However, similar genetic manipulations can be executed using other genetic systems. Also, any *S. sonnei* strain containing the form I plasmid can be used as a source of the form I antigenic genes and any *S. flexneri* IIa strain expressing type and group antigens can be used as a source of these antigenic genes. Likewise, virtually any strain of an enteric disease agent (e.g., an enterotoxigenic *E. coli* strain) can be used as the source of a protective antigenic gene, providing that the strain expresses the specific antigen of interest. Therefore, no singularly special strains or techniques, other than the galE *S. typhi* carrier strains or similarly attenuated non-reverting mutant *S. typhi* strains are needed to create a genetic hybrid *S. typhi* oral vaccine strain according to this invention.

The description of the subject invention includes detailed reference to specific embodiments to ensure a thorough understanding of the making and using thereof. It is to be understood, however, that these specific embodiments are considered merely exemplary of those within the scope of the invention defined by the claims which follow.

We claim:

1. A genetic hybrid derivative, having deposit accession number ATTC 31904, of an attenuated galactose epimeraseless mutant strain of *S. typhi* and a non-typhoid protective antigen carried thereby, wherein the non-typhoid protection antigen is the form I antigen of *Shigella sonnei* and the genetic hybrid derivative strain expresses both *S. typhi* and *S. sonnei* antigens.

2. A living attenuated oral vaccine, for the immunization against the enteric diseases bacillary dysentery and typhoid fever, comprising as the active component an effective dose of the genetic hybrid derivative of claim 1.

3. A genetic hybrid derivative, having deposit accession number ATCC 31931, of an attenuated galactose epimeraseless mutant strain of *S. typhi* and a non-typhoid protective antigen carried thereby, wherein the non-typhoid protective antigen is the *S. flexneri* IIa group (3, 4) and type antigens and the genetic hybrid derivative strain expresses both *S. typhi* and *S. flexneri* IIa (3,4) and type antigens.

4. A living attenuated oral vaccine, for the immunization against the enteric diseases bacillary dysentary and typhoid fever, comprising as the active component an effective dose of the genetic hybrid derivative of claim 3.

5. An oral vaccine according to claims 2 or 4 further comprising a pharmaceutical diluent.

6. An oral vaccine according to claims 2 or 4 in freeze-dried form.

7. A method of immunizing a susceptible host against the enteric diseases bacillary dysentary and typhoid fever comprising orally administering to said host a vaccine according to claims 2 or 4.

* * * * *